(12) United States Patent
Vrablic et al.

(10) Patent No.: US 7,416,750 B1
(45) Date of Patent: Aug. 26, 2008

(54) COMPOSITION TO PROVIDE MAINTENANCE AND NUTRITIONAL SUPPORT IN GLYCEMIC CONTROL DEFICITS

(75) Inventors: Angelica Vrablic, Boca Raton, FL (US); Glenn Schneider, Bohemia, NY (US); Robert Silverman, Bohemia, NY (US)

(73) Assignee: NBTY, Inc., Bohemim, NY (US)

( * ) Notice: Subject to any disclaimer, the term of this patent is extended or adjusted under 35 U.S.C. 154(b) by 0 days.

(21) Appl. No.: 11/710,893

(22) Filed: Feb. 26, 2007

(51) Int. Cl.
*A61K 36/54* (2006.01)
(52) U.S. Cl. ........................ 424/736; 424/767; 514/387
(58) Field of Classification Search ........................ None
See application file for complete search history.

(56) References Cited

U.S. PATENT DOCUMENTS

| | | | |
|---|---|---|---|
| 5,929,066 A * | 7/1999 | McCarty | ..................... 514/188 |
| 6,203,819 B1 | 3/2001 | Fine | |
| 6,485,760 B2 | 11/2002 | Matsuyama | |
| 6,551,627 B1 | 4/2003 | Yoon et al. | |
| 6,716,459 B2 | 4/2004 | Matsuyama | |
| 6,784,206 B2 | 8/2004 | Udell et al. | |
| 6,787,163 B2 | 9/2004 | Harris et al. | |
| 7,033,623 B2 | 4/2006 | Suzuki et al. | |
| 7,125,571 B2 | 10/2006 | Organ et al. | |
| 2002/0155163 A1 * | 10/2002 | Benjamin et al. | ........... 424/600 |
| 2004/0224035 A1 * | 11/2004 | Miller et al. | ................. 424/739 |
| 2005/0255215 A1 * | 11/2005 | Agarwala et al. | ........... 426/594 |

FOREIGN PATENT DOCUMENTS

JP    2002308766 A   * 10/2002

OTHER PUBLICATIONS

See http://www.gardfoods.com/coffee/coffee.plant.htm—accessed Nov. 8, 2007.*

* cited by examiner

*Primary Examiner*—Susan C Hoffman
(74) *Attorney, Agent, or Firm*—Lee Grosskreuz Hechtel

(57) ABSTRACT

A Composition to provide nutritional support for mammals having glycemic control and deficit concerns, and assist in managing glycemic controls deficits, with a synergistic combination of natural ingredients.

15 Claims, No Drawings

COMPOSITION TO PROVIDE MAINTENANCE AND NUTRITIONAL SUPPORT IN GLYCEMIC CONTROL DEFICITS

FIELD OF THE INVENTION

A composition useful for managing and providing nutritional support for glycemic balance and control deficits in animals, and particularly, in mammals, including humans.

BACKGROUND

Diabetes, metabolic syndrome, impaired glucose tolerance and related problems in glycemic control and management are tremendous public health concerns which affect millions of people in the United States and worldwide.

Diabetes is believed to have multiple etiologies including, inter alia, genetics, diet, exercise, sleep, caloric intake, trauma, infection, stress, drug use, and/or autoimmune reactions. Diabetes is generally classified into two general categories, where diabetes mellitus is typically known as type I diabetes due to insulin deficiency. Insulin is responsible for the regulation of a variety of metabolic functions, including the conversion of glucose to glycogen to lower the blood glucose level. Other forms of diabetes that can occur due to reduced insulin effectiveness in conjunction with other primary diseases are generally known as type II diabetes. Furthermore, diabetes is a chronic disease having a variety of pathological manifestations, and may be accompanied by disorders of lipid metabolism, circulation and glucose metabolism, among other effects.

In addition, aging may also cause a progressive loss of glucose tolerance possibly based on decreased insulin sensitivity in hypothalamic receptors and/or decreased response to glucose and insulin in the peripheral tissue. Should a glucose tolerance loss become pronounced, the condition would be diagnosed and treated as diabetes would be.

It would be highly advantageous to provide a composition that assists in managing glycemic control and levels with nutritional support beneficial for those affected by such deficits.

SUMMARY

A Composition of botanically-derived ingredients, naturally-occurring ingredients, including nopal, cinnamon, chlorogenic acid, biotin, and pantothenic acid, and extracts thereof, which may be formed into a dietary supplement product. The Composition may be used to provide nutritional support for mammals inflicted with glycemic level concerns and assist in managing glycemic control problems such as, for example, diabetes, metabolic syndrome, impaired glucose tolerance, and related glycemic deficits and problems.

DETAILED DESCRIPTION

This disclosure relates to a dietary supplement Composition for supporting positive health and bodily nutrition, and managing deficits in glycemic levels, or blood glucose (sugar) levels, in mammals. Deficits in glycemic control may include, for example, diabetes, metabolic syndrome, and related disorders or problems associated with glycemic control. This Composition includes a combination of naturally-occurring, botanically-derived ingredients, such as natural compounds and extracts having hypoglycemic properties, and vitamin components, which combine to produce synergistic and complementary beneficial effects in mammals. This Composition may also alleviate the various symptoms associated with glycemic deficits, by supporting and improving the general bodily health of a mammal suffering with such concerns.

The Composition is a synergistic combination of nopal, a species of Opuntia, also known as prickly pear cactus; cinnamon or cinnamon extract (Cinnamomum cassia); chlorogenic acid which is typically found in green coffee beans and berries; biotin; and pantothenic acid, each of which separately is known to positively affect glycemic control, and in combination provides additional positive synergistic effects.

Nopal, particularly the cactus petal portion of the plant, is widely used as a food in the Southwestern United States, Mexico, and other areas. It is also used as a folk remedy for glucose control in those areas. Nopal has high soluble fiber content and a high pectin content, which may slow intestinal glucose uptake and account, at least partially, for its hypoglycemic properties. Studies have found distinct improvements in diabetics after nopal ingestion, and the results suggest increased or enhanced insulin sensitivity. Importantly, no negative side effects have been found with nopal ingestion and use. The nopal petal also provides a rich source of vitamins A and C.

Cinnamon and cinnamon extract is obtained from the bark of the Cinnamomum cassia tree, and has long used a medicinal herb and a spice. Studies done by the U.S. Agricultural Research Services labs, and other labs, suggest that the cinnamon bark constituent, methylhydroxy chalcone polymer ("MHCP") may be effective in improving the responsiveness of peripheral tissues to insulin and positively supporting sugar metabolism overall within the body. MHCP is also known as type A procyanidin oligomers of catechins and epicatechins.

Biotin is a water-soluble B vitamin that is found in animals, plants and microorganisms that enhances the secretion of insulin in animals as well has playing an important role in the metabolism of fatty acids, sugars, and alpha-amino acids. Biotin supplementation has been shown to enhance insulin sensitivity and increase the activity of glucokinase, which activates the utilization of glucose by the liver. Biotin supplementation has also been shown to significantly reduce fasting blood glucose levels and improve blood glucose control in insulin dependent diabetes meliltus and non-insulin dependent diabetics in several studies.

Chlorogenic acid is a polyphenol found in berries, coffee (particularly green coffee beans), other foods, and their extracts. Studies have shown chlorogenic acid to be an inhibitor of hepatic glucose-6-phosphate translocase, and this enzyme is responsible for the production of endogenous glucose via gluconeogenesis and glycogenolysis, both of which are important in the homeostatic regulation of blood glucose levels. Inhibitors of glucose-6-phosphate translocase may assist in the reduction of the inappropriately high rates of hepatic glucose output, which is commonly found in non-insulin dependant diabetes.

Pantothenic acid, also known as vitamin B5, is a water-soluble vitamin that is essential to mammalian nutrition. Pantothenic acid is necessary to form coenzyme-A, and is important in a number of biological reactions, including the production of energy, the catabolism of fatty acids and amino acids, the synthesis of fatty acids, phospholipids, sphingolipids, cholesterol and steroid hormones, and the synthesis of heme and the neurotransmitter acetylcholine. It also appears to be involved in the regulation of gene expression and in signal transduction.

The novel Composition combines ingredients, all of which are naturally occurring, that synergistically retard intestinal glucose uptake, enhance glucose metabolism, enhance uptake by cells, and reduce inappropriately high hepatic glucose out. The Composition accomplishes these facets of glycemic control and nutritional support without negative side efforts, or negative ingredient interactions. The Composition may also be ingested with little or no interaction with traditional medications and medicaments.

The Composition may be formed into an easily ingestible supplement, such as, for example, capsules, tablets, powders, liquid concentrates, ready-made drinks, pastes and the like. In one embodiment, the Composition may be formed as a capsule for individual doses. The daily dosages for each ingredient of the Composition fall within the following approximate ranges: 1 g (gram) to 5 g of nopal or nopal extract; 100 mg (milligram) to 1 g of cinnamon or cinnamon extract; 50 mg to 300 mg of chlorogenic acid; 50 µg (microgram) to 200 µg of biotin; and 1 mg to 50 mg of pantothenic acid. Each of these ranges is within the approximate daily dosage for a mammal. These ingredients may be combined by any convenient or conventional means to a form useful for ingestion or bodily absorption. A capsule may be formed in any convenient size by any convenient method or conventional process, often formed in a 500 mg size for ease of swallowing.

Where a capsule is formed into a 500 mg size, a proper dosage level for a particular individual may include the ingestion of more than one capsule. A 500 mg capsule may include the Composition ingredients for combination in the approximate ranges of: 200 mg to 400 mg of nopal or nopal extract; 25 mg to 75 mg of cinnamon or cinnamon extract; 15 mg to 20 mg of chlorogenic acid; 25 µg to 75 µg of biotin; and, 1 mg to 4 mg of pantothenic acid. An individual may choose to ingest one or more capsules, or a plurality, as desired, according to the amount of Composition in each capsule.

In another embodiment, a capsule may be formed in any larger or smaller size, such as, for example, as a 750 mg size capsule. A capsule in a 750 mg size would include ingredients in the approximate general ranges of: 300 to 500 mg nopal or nopal extract; 50 to 150 mg cinnamon or cinnamon extract; 25 to 50 mg chlorogenic acid; 25 to 75 µg of biotin; and 1 to 4 mg pantothenic acid. A larger capsule size may be convenient to a typical user since generally one capsule could provide a daily dosage necessary to control glycemic deficits.

In alternative embodiments, the Composition may be formed within the approximate, general ranges of ingredients as a powder, a powder in a sachet, a tablet, a liquid concentrate, a ready-made drink, nutritional bars, dermal patches from absorption through the skin, or a paste format.

It will be appreciated that the novel Composition may be advantageously used by humans, and other mammals, as nutritional support to manage diabetes and other glycemic control problems without negative side effects or chemical interactions typically associated with traditional pharmaceuticals or medicines. In addition, the positive synergistic affects of the ingredients of the Composition provide greater benefits than single ingredients and/or previously known combinations. Therefore, the Composition may be readily used by those suffering with glycemic control problems and avoid further health issues caused by negative reactions and interactions that can often be debilitating for those having previously compromised general health.

It should be understood that the description and examples are only illustrative of the disclosure. Various alternatives and modifications can be devised by those skilled in the art without departing from the disclosure. Accordingly, the present disclosure is intended to embrace all such alternatives, modifications and variances which fall within the scope of the appended claims.

What is claimed is:

1. A dietary supplement Composition of botanically-derived ingredients, consisting of: nopal, cinnamon, chlorogenic acid, biotin, and pantothenic acid.

2. The dietary supplement Composition of botanically-derived ingredients of claim 1, wherein the dietary supplement Composition is formed into a capsule.

3. The dietary supplement Composition of botanically-derived ingredients of claim 2, wherein the amount of nopal in a dosage is in the range of 1 gram to 5 grams.

4. The dietary supplement Composition of botanically-derived ingredients of claim 3, wherein the amount of cinnamon in a dosage is in the range of 100 milligrams to 1 gram.

5. The dietary supplement Composition of botanically-derived ingredients of claim 4, wherein the amount of chlorogenic acid in a dosage is in the range of 50 milligrams to 300 milligrams.

6. The dietary supplement Composition of botanically-derived ingredients of claim 5, wherein the amount of biotin in a dosage is in the range of 50 micrograms to 200 micrograms.

7. The dietary supplement Composition of botanically-derived ingredients of claim 6, wherein the amount of pantothenic acid in a dosage is in the range of 1 milligram to 50 milligrams.

8. The dietary supplement Composition of botanically-derived ingredients of claim 1, wherein the amount of nopal in a dosage is in the range of 300 milligrams to 500 milligrams.

9. The dietary supplement Composition of botanically-derived ingredients of claim 8, wherein the amount of nopal in a dosage is in the range of 200 milligrams to 400 milligrams.

10. The dietary supplement Composition of botanically-derived ingredients of claim 8, wherein the amount of cinnamon in a dosage is in the range of 50 milligrams to 150 milligrams.

11. The dietary supplement Composition of botanically-derived ingredients of claim 8, wherein the amount of cinnamon in a dosage is in the range of 25 milligrams to 75 milligrams.

12. The dietary supplement Composition of botanically-derived ingredients of claim 8, wherein the amount of chlorogenic acid in a dosage is in the range of 25 milligrams to 50 milligrams.

13. The dietary supplement Composition of botanically-derived ingredients of claim 8, wherein the amount of chlorogenic acid in a dosage is in the range of 15 milligrams to 20 milligrams.

14. The dietary supplement Composition of botanically-derived ingredients of claim 8, wherein the amount of biotin in a dosage is in the range of 25 micrograms to 75 micrograms.

15. The dietary supplement Composition of botanically-derived ingredients of claim 8, wherein the amount of pantothenic acid in a dosage is in the range of 1 milligram to 4 milligrams.

* * * * *